United States Patent [19]

Akhavi

[11] 4,266,558
[45] May 12, 1981

[54] METHOD OF COLLECTING AND DISPENSING A BLOOD SAMPLE

[75] Inventor: David S. Akhavi, Los Angeles, Calif.

[73] Assignee: American Hospital Supply Corporation, Evanston, Ill.

[21] Appl. No.: 25,979

[22] Filed: Apr. 2, 1979

[51] Int. Cl.³ ............................................... A61B 5/14
[52] U.S. Cl. .................................... 128/766; 128/767; 73/425.4 P
[58] Field of Search ......................... 128/763–771; 210/DIG. 23, DIG. 24; 73/425.4 P, 425.6

[56] References Cited

U.S. PATENT DOCUMENTS

| 2,848,999 | 8/1958 | McGrew | 128/767 |
|---|---|---|---|
| 3,062,202 | 11/1962 | Hyman et al. | 128/2.05 |
| 3,157,481 | 11/1964 | Bujan | 55/417 |
| 3,276,447 | 10/1966 | Hamilton | 128/214 |
| 3,322,114 | 5/1967 | Portnoy et al. | 128/2 |
| 3,585,647 | 6/1971 | Gajewski et al. | 3/1 |
| 3,698,561 | 10/1972 | Babson | 210/DIG. 24 X |
| 3,768,978 | 10/1973 | Grubb et al. | 128/768 X |
| 3,785,367 | 1/1974 | Fortin et al. | 128/2 F |
| 3,867,923 | 2/1975 | West | 128/766 |
| 3,890,956 | 6/1975 | Moorehead | 128/2 F |
| 3,930,492 | 1/1976 | Hatsuno et al. | 128/2 F |
| 3,942,514 | 3/1976 | Ogle | 128/2 F |
| 3,960,139 | 6/1976 | Bailey | 128/765 X |
| 3,965,889 | 6/1976 | Sachs | 128/767 X |
| 3,978,846 | 9/1976 | Bailey | 128/755 X |
| 4,043,335 | 8/1977 | Ishikawa | 128/218 N |
| 4,085,737 | 4/1978 | Bordow | 128/763 |
| 4,133,304 | 1/1979 | Bailey | 128/764 |
| 4,187,861 | 2/1980 | Heffernan | 128/767 X |

FOREIGN PATENT DOCUMENTS

| 353916 | 6/1961 | Switzerland | 128/763 |
|---|---|---|---|
| 864007 | 3/1961 | United Kingdom | |

OTHER PUBLICATIONS

*British Med. Journ.*, Aug. 28, 1971, vol. 3, pp. 512–516.
*American Rev. of Resp. Dis.* vol. 115, 1977, pp. 1061–1063.
*Anesthesia and Intensive Care*, vol. VI, No. 3, Aug. 1978, pp. 251–255.

Primary Examiner—Kyle L. Howell
Attorney, Agent, or Firm—Larry N. Barger

[57] ABSTRACT

A method of collecting a blood sample, such as from an artery, in a flexible tube collector while forcing at least a portion of the air in the collector through a "nonwet" filter by means of blood pressure. This nonwet filter prevents escape of blood from the collector. The blood containing blood sampler can then be chilled in an ice bath if a test is not run immediately, and then the test sample dispensed to a machine for testing the partial pressure oxygen and carbon dioxide in the blood. If the machine does not have a vacuum extractor, blood can be stripped from the tube by a movable clamp structure.

18 Claims, 6 Drawing Figures

METHOD OF COLLECTING AND DISPENSING A BLOOD SAMPLE

BACKGROUND

There have been many problems with collecting blood samples, such as from an artery, so that there is minimal error in tests for partial pressures of oxygen and carbon dioxide in the blood sample. There has also been some problems in clearly distinguishing between arterial and venous blood when collecting the sample.

In my co-pending application entitled "Blood Sampler," Ser. No. 025,980, filed Apr. 2, 1979, I describe a unique flexible tube blood collector which has specific advantages for collecting arterial blood. The present application deals with the unique method of collecting blood with such a blood sampler.

A related co-pending application entitled "Stripper Clamp," invented by David S. Akhavi, Ser. No. 026,117, filed Apr. 2, 1979, relates to the specific structure of a clamp used in the method of collecting and dispensing a blood sample according to the present method.

SUMMARY OF THE INVENTION

The present invention has to do with a method of collecting a blood sample, such as from an artery, in a flexible tube reservoir and forcing air from the reservoir out through a nonwet filter valve by means of blood pressure. The flexible tube is pinched off by means of a clamp to segment an air contaminated portion of the blood sample from a test portion of the blood sample. If a test is not immediately performed on the blood, it is chilled to prevent blood from continuing to metabolize oxygen and cause an erroneous test. The test portion of the blood sample is dispensed to a testing machine. If such machine does not have a vacuum extractor, blood is dispensed by pinchingly stripping the flexible tube with a sliding or rolling clamp structure.

THE DRAWINGS

DETAILED DESCRIPTION

Figure 1:
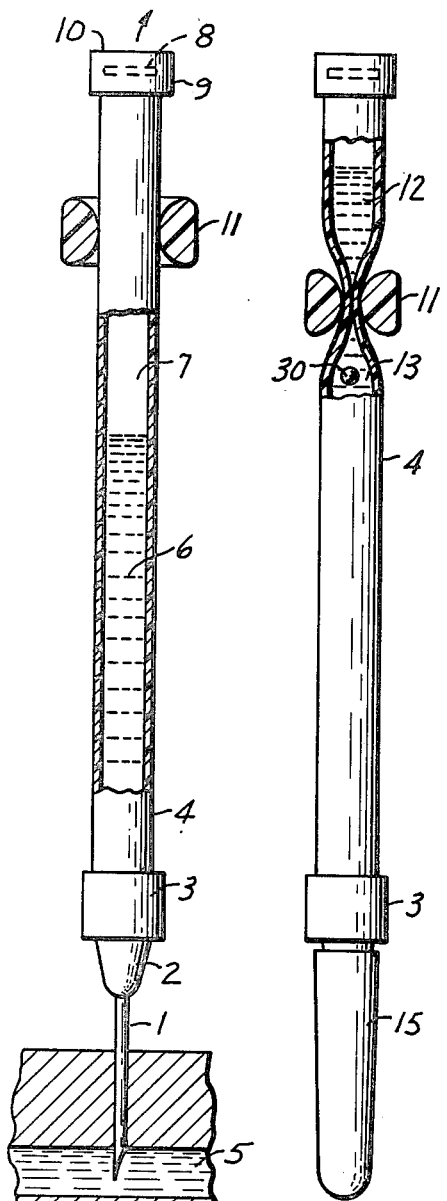
FIG. 1 is a front elevational view of a blood sampler in the process of collecting a blood sample.
Figures 2, 3:
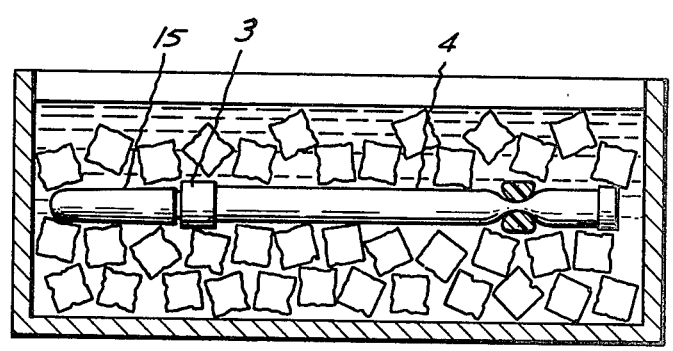
FIG. 2 is a front elevational view of the blood sampler after the blood has been collected and the sampler pinched to segment the two portions of blood.
FIG. 3 is a front elevational view of the blood sampler being chilled in an ice bath.
Figure 4:
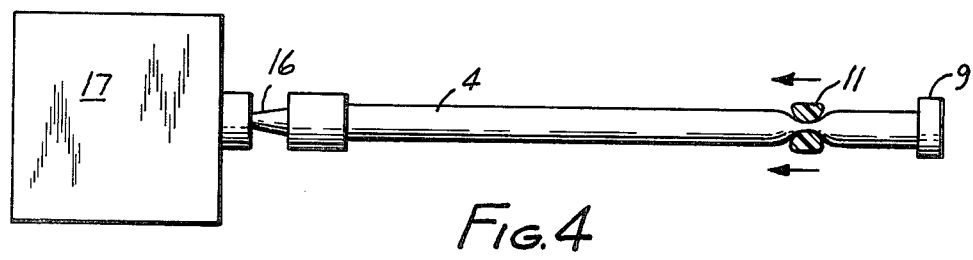
FIG. 4 is a front elevational view of the blood sampler in horizontal position dispensing a sample to a testing machine with a slide clamp.

In FIG. 1, a needle that includes a cannula 1 and a hub 2 is connected through a needle adapter 3 to an inlet of a flexible tubular reservoir 4. The needle is shown here injected into a patient's artery 5. Arterial blood pressure causes a blood sample 6 to well up in tubular reservoir 4 and expel overriding air 7 through an outlet having a nonwet filter vent 8 in a filter housing 9. Arterial blood is visually distinguished from venous blood by its fast flow rate and pulsations. FIG. 1 shows a first embodiment of a filter housing 9 which has a generally flat exterior surface 10 that is not adapted to receive a syringe tip. A sliding clamp 11 with opposed openable and closable jaws is loosely fit on tubular reservoir 4 in FIG. 1. In FIG. 2, the jaws of the clamp have been pinched together to segregate the samples, and FIG. 4 shows how the rounded inner surfaces of the opposed jaws can slide along the tube stripping out the blood sample.

In FIG. 2, the blood sample has been collected and clamp 11 moved downwardly on tubular reservoir 4 where it pinches the tube shut between the tube's inlet and outlet to segment an air contaminated blood sample portion 12 from a testing portion 13 of the sample. After collecting a sample, it is normal to stick the needle in a rubber stopper or replace the needle with a syringe tip cap (not shown to retain the blood. In FIG. 2, a protector 15 has been placed on the needle, and the rubber stopper could be inside this protector, if desired.

When an arterial blood sample is taken, it is usually tested for the partial pressure of oxygen and carbon dioxide. If the sample taken cannot be tested immediately, it is chilled in an ice bath, such as shown in FIG. 3, to prevent the continual metabolizing of oxygen by the blood sample. The time lag between blood sample collection and blood testing might occur where the testing facilities are overloaded with blood samples or there is a considerable distance between the patient and the testing lab.

Once the blood sample is ready for testing, the protector 15 and needle are removed to expose a needle adapter 16 which can connect directly to a blood testing machine 17. Normally, such machine has a small probe that extends inside needle adapter 16 to suck out a measured quantity of the blood sample. In some machines which do not have a vacuum extractor, the blood sample can be slidingly stripped by moving clamp 11 in a forward longitudinal direction along the flexible tubular reservoir 4. As this is done, air is drawn in through the nonwet filter in the filter adapter 9.

Figure 5:
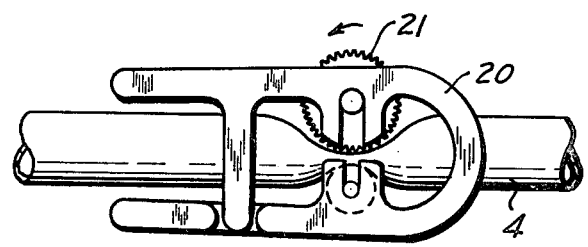
FIG. 5 is a side elevational view of a type of roller clamp that can be used for strippingly dispensing blood from the sampler.

The clamp 11, shown schematically in FIG. 4, is a sliding type clamp. An alternate clamp is shown in FIG. 5, which is a roller type clamp with a body 20 and a thumb actuated roller 21 that moves the clamp longitudinally along the flexible tubular reservoir 4. The details of this clamp structure to form this stripping action, as well as the opening and closing action for pinching the reservoir as in FIG. 2, is the subject of a co-pending application, identified at the beginning of this specification.

Figure 6:
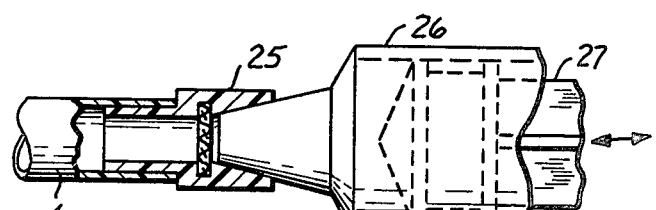
FIG. 6 is a sectional view of an alternative embodiment of a nonwet filter housing for connecting with a syringe to apply vacuum or pressure to the blood sampler.

While the preferred method of collecting a blood sample includes the pinching off of the air contaminated blood sample in a forward chamber of the blood collector, an alternate structure of the filter adapter 25 can have an internally tapered section for connecting to a syringe 26. By pushing a plunger 27 to the left in FIG. 6, a pressure can be created inside of tubular reservoir 4 to force the blood sample into the testing machine 17. However, this has the disadvantage of introducing additional air into the blood sample. Such a syringe attachment can also be used for applying a vacuum by moving plunger 27 to the right of FIG. 6 to aid in collecting a venous blood sample which has reduced pressure.

To aid in mixing the blood sample 13 in FIG. 2 with a dry heparin coating, an optional steel ball 30 can be included in the blood collector and mixing accelerated by shaking or rotating the blood sampler.

The flexible tube permits quick mixing of the dry heparin and blood, as well as remixing any separated plasma and hemoglobin by squeezing or rolling between the operator's hands with a squeezing and ovaling action between the tube's inlet and outlet. It is currently recommended to vigorously roll rigid syringe-type blood samplers 50 times to remix separated plasma and hemoglobin.

In the foregoing description, specific examples have been used to describe the invention. However, it is understood by those skilled in the art that certain modifications can be made to these examples without departing from the spirit and scope of the invention.

I claim:

1. A method of collecting an arterial blood sample comprising the steps of:
    (a) puncturing an artery with a needle attached to an inlet of a reservoir containing a gas, which reservoir has an outlet;
    (b) forcing at least a portion of the gas out of the outlet with arterial blood pressure while maintaining a collected arterial blood sample confined within the reservoir; and
    (c) closing the reservoir at a location between the reservoir's inlet and outlet to segment the collected blood sample.

2. A method as set forth in claim 1, wherein the reservoir is flexible and the blood sample is segmented by pinching the reservoir shut at a particular location.

3. A method as set forth in claim 2, wherein the reservoir is an elongated tube and the tube is closed with a pinch clamp on the tube.

4. A method as set forth in claim 1, wherein the method includes the further step of dispensing one of the segmented samples to a testing machine.

5. A method as set forth in claim 4, wherein there is a first sample adjacent the vent and a second sample adjacent the needle, and this second sample is dispensed to a testing machine.

6. A method as set forth in claim 1, wherein the method includes placing the blood containing reservoir in a chilled environment.

7. A method as set forth in claim 6, wherein the chilled environment is an ice bath.

8. A method as set forth in claim 1, wherein the method includes the further step of stripping the blood from the reservoir.

9. A method as set forth in claim 8, wherein the reservoir is an elongated flexible tube and the stripping step is carried out by moving a clamp along the tube.

10. A method as set forth in claim 9, wherein the clamp is moved along the tube with a sliding motion.

11. A method as set forth in claim 9, wherein the clamp has a roller and the clamp is moved along the tube by rotating the roller.

12. A method as set forth in claim 9, wherein a common clamp is used for both segmenting the blood sample and stripping the tube.

13. A method as set forth in claim 1, wherein the reservoir is transparent and the method includes the step of visually determining that an artery has been punctured by the blood flow rate and pulsations into the reservoir.

14. A method as set forth in claim 1, wherein the collected blood is mixed by squeezingly rolling the tube between two objects.

15. A method as set forth in claim 14, wherein the objects are an operator's hands.

16. A method of collecting an arterial blood sample comprising the steps of:
    (a) puncturing an artery with a needle attached to an inlet of a reservoir containing a gas, which reservoir has an outlet and a valve at such outlet;
    (b) forcing at least a portion of the gas out of the outlet with arterial blood pressure;
    (c) contacting the outlet's valve with the blood, which valve prevents the blood from exiting through the outlet; and
    (d) closing the reservoir at a location between the reservoir's inlet and outlet to segment the collected blood sample.

17. A method of collecting a blood sample comprising the steps of:
    (a) puncturing a blood conduit with a needle attached to an inlet of a reservoir containing a gas, which reservoir has an outlet;
    (b) forcing at least a portion of the gas out of the outlet with blood pressure while maintaining the collected blood sample confined within the reservoir; and
    (c) closing the reservoir at a location between the reservoir's inlet and outlet to segment the collected blood sample.

18. A method of collecting and mixing a blood sample comprising the steps of:
    (a) puncturing a blood conduit with a needle attached to an inlet of a flexible tube containing a gas, which flexible tube has an outlet;
    (b) transferring at least a portion of the gas from an interior of the flexible tube through the tube's outlet; and
    (c) ovaling the tube at a location between its inlet and outlet with a rolling squeezing motion to mix the tube's contents.

* * * * *